United States Patent
Yao et al.

(10) Patent No.: US 12,016,628 B2
(45) Date of Patent: Jun. 25, 2024

(54) OPTICAL COHERENCE TOMOGRAPHY (OCT) SYSTEM AND METHOD THAT MEASURE STIMULUS-EVOKED NEURAL ACTIVITY AND HEMODYNAMIC RESPONSES

(71) Applicant: THE BOARD OF TRUSTEES OF THE UNIVERSITY OF ILLINOIS, Urbana, IL (US)

(72) Inventors: Xincheng Yao, Hinsdale, IL (US); Tae Yun Son, Chicago, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 927 days.

(21) Appl. No.: 16/497,071

(22) PCT Filed: Mar. 27, 2018

(86) PCT No.: PCT/US2018/024534
§ 371 (c)(1),
(2) Date: Sep. 24, 2019

(87) PCT Pub. No.: WO2018/183304
PCT Pub. Date: Oct. 4, 2018

(65) Prior Publication Data
US 2020/0375452 A1    Dec. 3, 2020

Related U.S. Application Data

(60) Provisional application No. 62/477,134, filed on Mar. 27, 2017.

(51) Int. Cl.
*A61B 3/10*     (2006.01)
*A61B 3/00*     (2006.01)
(Continued)

(52) U.S. Cl.
CPC ............ *A61B 3/102* (2013.01); *A61B 3/0008* (2013.01); *A61B 3/0025* (2013.01);
(Continued)

(58) Field of Classification Search
CPC .... A61B 3/00; A61B 3/10; A61B 3/12; A61B 3/14; A61B 3/102; A61B 3/103;
(Continued)

(56) References Cited

U.S. PATENT DOCUMENTS

| | | | |
|---|---|---|---|
| 7,301,644 B2 * | 11/2007 | Knighton | G01B 9/02089 |
| | | | 356/479 |
| 2004/0215293 A1 | 10/2004 | Eells et al. | |

(Continued)

OTHER PUBLICATIONS

International Search Report issued for application PCT/US2018/024534, dated Aug. 7, 2018.
(Continued)

*Primary Examiner* — Jie Lei
(74) *Attorney, Agent, or Firm* — Thomas | Horstemeyer, LLP

(57) ABSTRACT

A multi-modal functional OCT imaging methodology and system are provided that enable concurrent intrinsic optical signal (IOS) imaging of stimulus-evoked neural activity and hemodynamic responses at capillary resolution. An OCT angiography (OCTA)-guided IOS analysis is used to separate neural-IOS and hemodynamic-IOS changes in the same retinal image sequence. The OCTA-guided IOS data processing used for this purpose differentiates two functional images, namely, a neural-IOS map and a hemodynamic-IOS map, from the same image dataset.

12 Claims, 8 Drawing Sheets

(51) Int. Cl.
*A61B 3/12* (2006.01)
*G01J 3/02* (2006.01)
*G01J 3/45* (2006.01)
*G06T 7/10* (2017.01)

(52) U.S. Cl.
CPC .......... *A61B 3/1241* (2013.01); *G01J 3/0208* (2013.01); *G01J 3/45* (2013.01); *G06T 7/10* (2017.01); *G01J 2003/451* (2013.01); *G06T 2207/10101* (2013.01); *G06T 2207/30041* (2013.01); *G06T 2211/404* (2013.01); *G06T 2219/021* (2013.01)

(58) Field of Classification Search
CPC ... A61B 3/0008; A61B 3/0025; A61B 3/0066; A61B 3/117; A61B 3/1173; A61B 3/1233; A61B 3/1241; G06T 7/10; G06T 2207/10101; G06T 2207/30041; G06T 2211/404; G06T 2219/021; G01J 3/02; G01J 3/0208; G01J 3/45; G01J 2003/451
USPC ....... 351/206, 205, 208, 210–212, 221, 246; 356/479, 497, 498
See application file for complete search history.

(56) References Cited

U.S. PATENT DOCUMENTS

| | | |
|---|---|---|
| 2013/0301008 A1 | 11/2013 | Srivastava et al. |
| 2015/0018665 A1 | 1/2015 | Jasanoff et al. |
| 2015/0272438 A1 | 10/2015 | Yao et al. |
| 2016/0367145 A1* | 12/2016 | Lasser .................. A61B 5/0048 |

OTHER PUBLICATIONS

Biesecker et al., Glial cell calcium signaling mediates capillary regulation of blood flow in the retina. J Neurosci 36, 9435-9445, (2016).

Lu et al., Stimulus-evoked outer segment changes occur before the hyperpolarization of retinal photoreceptors. Biomed Opt Express 8, 38-47, (2017).

Wang et al., Functional optical coherence tomography reveals transient phototropic change of photoreceptor outer segments. Opt Lett 39, 6923-6926, (2014).

Newman, Functional hyperemia and mechanisms of neurovascular coupling in the retinal vasculature. J Cereb Blood Flow Metab 33, 1685-1695, (2013).

Palkovits et al., Relation of retinal blood flow and retinal oxygen extraction during stimulation with diffuse luminance flicker. Sci Rep 5, 18291, (2015).

Son et al., Optical coherence tomography angiography of stimulus evoked hemodynamic responses in individual retinal layers. Biomed Opt Express 7, 3151-3162, (2016).

Wang et al., In vivo optical coherence tomography of stimulus-evoked intrinsic optical signals in mouse retinas. J Biomed Opt 21, 96010, (2016).

* cited by examiner

OPTICAL COHERENCE TOMOGRAPHY (OCT) SYSTEM AND METHOD THAT MEASURE STIMULUS-EVOKED NEURAL ACTIVITY AND HEMODYNAMIC RESPONSES

CROSS-REFERENCE TO RELATED APPLICATIONS

The present application is a 35 U.S.C. 371 national stage application of, and claims priority to and the benefit of the filing date of, PCT Application No. PCT/US2018/024534 filed Mar. 27, 2018 entitled "AN OPTICAL COHERENCE TOMOGRAPHY (OCT) SYSTEM AND METHOD THAT MEASURE STIMULUS-EVOKED NEURAL ACTIVITY AND HEMODYNAMIC RESPONSES," which claims the benefit of and priority to the filing date of U.S. provisional application Ser. No. 62/477,134, filed on Mar. 27, 2017 and entitled "OPTICAL COHERENCE TOMOGRAPHY ANGIOGRAPHY OF STIMULUS EVOKED HEMODYNAMIC RESPONSES IN INDIVIDUAL RETINAL LAYERS," both of which are hereby incorporated by reference herein in their entireties.

GOVERNMENT RIGHTS STATEMENT

This invention was made with government support under grant Nos. R01 EY023522, R01 EY024628, and NIH P30 EY001792 awarded by the National Institutes of Health and under grant no. CBET-1055889, awarded by the National Science Foundation. The government has certain rights in this invention.

BACKGROUND

Neural activity in a localized brain region leads to rapid blood flow changes in that region. This phenomenon, called neurovascular coupling, also exists in the retina, which is part of the central nervous system. The retina consists of multiple functional layers, which contain cell bodies, plexiform layers with axons and dendrites to form the neuronal network that preprocesses light-evoked signals before transmission to the brain. This neuronal network is responsible for capturing light photons, converting light energy to bioelectrical activities, and conducting preliminary processing of visual information before transmission to the brain. Different eye diseases can target different retinal layers and induce morphological abnormalities and physiological dysfunctions. The major retinal diseases, such as retinitis pigmentosa (RP), age-related macular degeneration (AMD), glaucoma, and diabetic retinopathy (DR), or endothelial dysfunction secondary to systemic diseases are usually localized to one of these layers and induce morphological abnormalities, impaired neural and physiological responses and blood vascular system damage.

However, details of distortions in retinal neurovascular coupling (i.e., coherent interaction between retinal neural physiology and blood vascular system) associated with these major eye diseases are not well understood due to the limitation of existing techniques.

Many techniques have been used to evaluate retinal neurovascular coupling such as fundus photography, blue field simulation, pulsed Doppler sonography, color Doppler imaging, laser Doppler velocimetry (LDV), laser Doppler flowmetry, scanning laser Doppler flowmetry, speckle flowgraphy, and dynamic vessel analyzer. Each technique has limitations such as requiring repositioning of the transducer after light stimulation, surface imaging, dye injection, or long acquisition time. Moreover, none of these methods can provide necessary axial resolution to differentiate individual retinal layers.

By providing excellent axial resolution, optical coherence tomography (OCT) provides a noninvasive method for depth-resolved visualization of biological structures with micrometer-level resolution. OCT has been extensively used for depth-resolved examination of retinal morphology and physiology. OCT angiography, as a functional extension of OCT, allows three-dimensional (3D) and label-free mapping of vascular structures. Several techniques have been developed for the quantification of retinal blood flow using OCT angiography such as speckle variance (SV), phase variance (PV), optical microangiography (OMAG), split spectrum amplitude-decorrelation (SSAD), and correlation mapping (CM). Unlike conventional Doppler OCT or LDV which measure large retinal vessels (arteries and veins) to obtain total retinal blood flow, OCT angiography is capable of measuring both macro- and micro-circulation (down to capillaries). This allows OCT angiography to evaluate the microcirculation of specific regions of the retina, which would not be possible using other techniques that measure total retinal blood flow only.

Neural activity increases when it is subjected to flickering stimulation in retina. Blood flow responses to flicker light stimulation is altered in patients with vascular disease and that measurement of flicker-induced vasodilatation is a tool to monitor functional microvascular alterations.

Several previous studies have assessed the relation of flicker light stimulation and retinal hemodynamic response using various techniques. Recently, OCT angiography has been used for imaging the hemodynamic response caused by flicker light stimulation. In these studies, OCT en-face images were used to show retinal blood flow changes induced by light stimulation and to provide geometrical information about the blood flow changes from the entire retina.

Studies have not been performed that show depth-resolved information at individual retinal layers. Furthermore, there is no information on time-resolved hemodynamics changes caused by flicker light stimulation.

Neurodegenerative diseases are the major cause of dementia. In the USA and other developed countries, one of four persons with ages above 55 years may develop dementia. Early detection of these neurodegenerative diseases is essential for better study and development of preventive strategies. Neurovascular coupling reflects the spatial and temporal relationships between transient neural activity and hemodynamic responses (i.e., blood flow/oxygen dynamics), which is essential to maintain normal function of the central nervous system (CNS). Neurovascular coupling dysfunctions accompany neurodegenerative diseases. A recent diffusion functional magnetic resonance imaging (MRI) study has revealed impaired hemodynamic responses beyond the microinfarct core.

There is ample evidence to support that functional imaging of neurovascular coupling, i.e., spatiotemporal mapping of transient neural activity related hemodynamic responses, promises early detection of neurodegenerative diseases. However, direct access to the brain for high-resolution examination of neurovascular coupling defects is difficult. As part of the CNS, retinal microvasculature distortions were observed to correlate with neurodegenerative diseases. Given the light transparent property of the eye, high-resolution optical imaging of the retinal neural tissue and microvasculature is readily available. Therefore, the retina provides a unique window to investigate dementia, stroke, and other brain diseases at high resolution.

However, there is no established method to provide spatiotemporal resolution for functional assessment of coherent interactions between neural activity and hemodynamic changes at the level of individual capillaries, which directly interact with retinal neurons within individual layers in the retina. To date, most reported retinal imaging studies have been limited to morphological measurement of retinal cells and the retinal vasculature, such as the retinal vascular caliber, tortuosity, fractal dimension, branching, etc. Existing methods, such as electroretinogram (ERG) measurement for objective evaluation of retinal neural function, cannot match the resolution provided by a retinal imager. It is complicated to establish a correlation between outcomes from different instruments, especially in the complex retinal neurovascular network that consists of multiple retinal layers.

A need exists for a new imaging system and method that allow concurrent imaging of stimulus-evoked neural activity and hemodynamic responses in individual retinal layers. Such concurrent imaging ability facilitates early detection of neural degeneration and reliable assessment of treatment outcomes.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

The inventive principles and concepts are directed to a new imaging system and method that allow concurrent imaging of stimulus-evoked neural activity and hemodynamic responses in individual retinal layers.

Quantitative evaluation of retinal neurovascular coupling is needed for a better understanding of visual function and early detection of eye diseases. However, there is currently no established method to monitor coherent interactions between stimulus-evoked neural activity and hemodynamic responses at high resolution. To fulfill that need, in accordance with an embodiment, a multi-modal functional OCT imaging methodology and system are provided that enable concurrent intrinsic optical signal (IOS) imaging of stimulus-evoked neural activity and hemodynamic responses at capillary resolution.

In accordance with this embodiment, an OCT angiography (OCTA)-guided IOS analysis is used to separate neural-IOS and hemodynamic-IOS changes in the same retinal image sequence. The OCTA-guided IOS data processing used for this purpose differentiates two functional images, namely, a neural-IOS map and a hemodynamic-IOS map, from the same image dataset. Frequency flicker stimuli-evoked neural-IOS changes occur in the outer retina (i.e., photoreceptor layer, first) and then in the inner retina, including in the outer plexus layer (OPL), the inner plexiform layer (IPL), and the ganglion cell layer (GCL)). The neural-IOS changes are followed by the occurrence of hemodynamic-IOS changes primarily in the inner retina (i.e., OPL, IPL, and GCL). Different time courses and signal magnitudes of hemodynamic-IOS responses are observed in blood vessels with various diameters.

Figure 1:
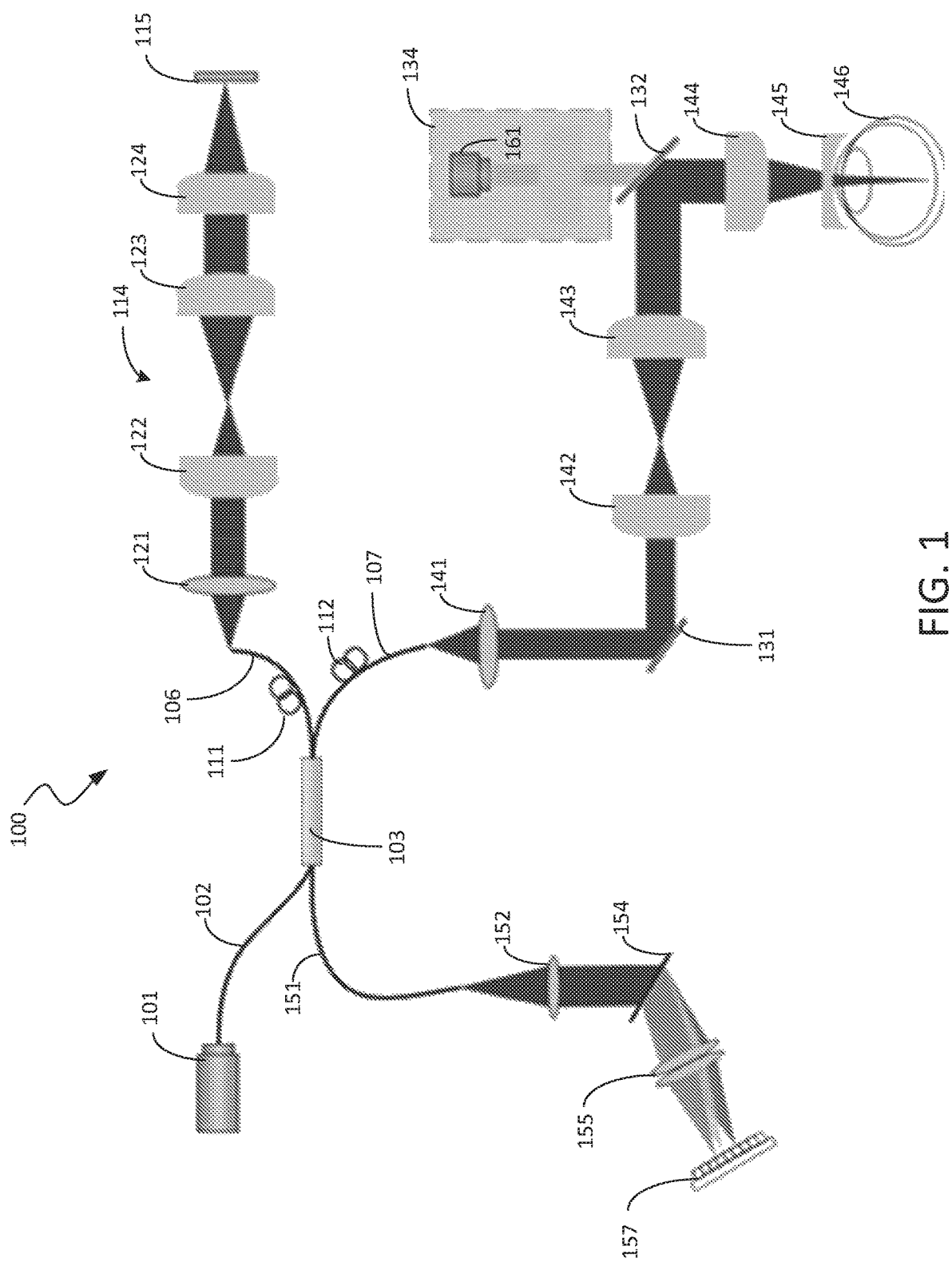
FIG. 1 is a schematic diagram of an OCT system 100 in accordance with a representative embodiment.

FIG. 1 is a schematic diagram of an OCT system 100 in accordance with a representative embodiment. The OCT system 100 is essentially an interferometer that relies on interference between a sample light beam and a reference light beam to create an interference pattern that can be analyzed to make the determinations about the neural- and hemodynamic-IOS changes described herein. Because the manner in which interferometers are used in OCT systems to produce two- and three-dimensional images of a sample is well known, a detailed discussion of the nature of the interferometer and the manner in which it operates is not provided herein in the interest of brevity. A light source 101, which is typically a low-coherence light source such as a broadband superluminescent diode (SLD), for example, produces a first light beam that travels along a first length of optical fiber 102 to a fiber coupler 103. The fiber coupler 103 includes a beam splitter (not shown) that splits the first light beam into a reference light beam and a sample light beam that are coupled onto second and third lengths of optical fiber 106 and 107, respectively, that include respective polarization controllers (PCs) 111 and 112, respectively.

The arm of the interferometer that includes the second length of fiber 106 and the PC 111 is the reference arm. The arm of the interferometer that includes the third length of fiber 107 and the PC 112 is the sample arm. The reference arm includes a lens system 114 and a mirror 115. The lens system can have a variety of configurations of various types of optical elements. In accordance with this representative embodiment, the lens system includes a first, second, third and fourth lenses 121, 122, 123 and 124, respectively. As shown in FIG. 1, these lenses perform various collimating and focusing functions on the reference light beam passing out of the end of the second length of optical fiber 106 and reflected from the mirror 115.

The arm of the interferometer that includes the third length of fiber 107 and the PC 112 is the sample arm. The sample arm includes a lens system, two scanning mirrors 131, a dichroic mirror 132, and a retinal stimulator 134. The lens system of the sample arm can have a variety of configurations of various types of optical elements. In accordance with this representative embodiment, the lens system of the sample arm includes a first, second, third, fourth, and fifth lenses 141, 142, 143, 144 and 145, respectively. As shown in FIG. 1, these lenses perform various collimating and focusing functions on the sample light beam passing out of the end of the third length of optical fiber 107 and reflected from the sample 146.

The reference and sample light beams reflected by the mirror 115 and by the sample 146, respectively, are combined in the optical coupler 103 and the combined signal is coupled into an end of a fourth length of optical fiber 151. The combined signal passing out of the opposite end of the fourth length of optical fiber 151 is collimated by a collimating lens 152 and the collimated light beam is directed onto a diffraction grating 154 that performs wavelength division demultiplexing to separate the light into different wavelengths of light. The different wavelengths of light are directed by lenses 155 onto different areas of a sensor array 157, which, in accordance with this representative embodiment, is a charge coupled device (CCD) camera. The diffraction grating 154, the lenses 155 and the sensor array 157 form a spectrometer. The scanning mirrors 131 have the effect of producing three-dimensional images on the sensor array 157.

In accordance with this representative embodiment, the retinal stimulator 134 comprises an light emitting diode (LED) 161 that generates visible light flicker stimuli in the form of a light pulse (e.g., 100 ms, duty ratio 50%, 10 Hz, 5 s duration, 504±13.5 nm, approximately 460 lux at the corneal surface). An example of a suitable LED for this purpose is a green LED having a peak wavelength of 505 nm (e.g., part number M505L3, sold by Thorlabs). The retinal stimulator 134 may include a collimating lens that couples the light pulse onto the dichroic mirror 132. The LED 161 is driven by a suitable driver circuit synchronized with the OCT system 100. A suitable drive circuit for this purpose is a T-Cube LED driver offered by Thorlabs of Newton, New Jersey as part number LEDD1B, which can be configured to provide a light pulse having a desired frequency, duty cycle and pulse width (e.g., 100 ms, duty ratio 50%, 10 Hz, 5 s duration).

The light source 101 may be, for example, a broadband SLD having part number D-840-HP-I sold by Superlum of Cork, Ireland. This particular SLD has a central wavelength of 850 nanometers (nm) and a bandwidth of 100 nm was used. The fiber coupler 103 may have a splitting ratio of, for example, 75:25 divided to the sample arm and reference arm, respectively. In some embodiments, the reference arm includes a variable neutral density filter (not shown) to adjust the light intensity from the reference arm and a glass plate (not shown) to compensate for the dispersion of optical components in the sample arm. The two scanning mirrors 131 may be, for example, scanning mirrors having part number 6231H, sold by Cambridge Technology, Inc. of Bedford, MA, USA). The scanning mirrors 131 are typically conjugated to the pupil of the eye to minimize the vignetting effect. The diffraction grating 154 may be, for example, a 1200 line/mm transmission grating sold by Wasatch Photonics of West Logan, UT, USA. The lenses 155 may be, for example, achromatic doublet lenses, f=300 mm. The sensor array 157 may be, for example, a line CCD camera with 2,048 pixels and a pixel size of 14×28 μm with a line rate up to 70,000 Hz.

In order to demonstrate the manner in which the OCT system 100 may be operated and the manner in which the methodology may be performed, an experiment that was conducted using mice and the results of the experiment will now be described.

All animal care and the experiment was performed in accordance with the Association for Research in Vision and Ophthalmology statement for the use of animals in ophthalmic and vision research. The experiment was performed following the protocols approved by the Animal Care Committee at the University of Illinois at Chicago. Seven adult wild-type mice (either sex, aged 8-10 weeks, weight 25-35 g, housed with a 12-h light-dark cycle) were used in this study. The strain was C57BL/6J and all mice were acquired from the Jackson Laboratory (Bar Harbor, ME, USA).

Before performing an OCT recording with the OCT system 100, the mice were anesthetized with a mixture of ketamine and xylazine (60 mg/kg and 3 mg/kg body weight, respectively) injected intraperitoneally. A heating pad was used to maintain body temperature during the experiment. A custom-designed animal holder with an ear/bite was used to minimize movements caused by breathing and heartbeat and to achieve six axis stages for precise and rapid positioning of the retinal area for imaging. The pupil was fully dilated with phenylephrine hydrochloride 2.5% and tropicamide 1%. A cover glass, along with GenTeal eye gel (Alcon Laboratories, Fort Worth, TX, USA), was placed on the cornea to prevent drying and to serve as a contact lens to improve the image quality by reducing optical aberrations of the eye.

For experimental purposes, the axial and lateral resolution values of the OCT system 100 were theoretically estimated at 3 μm and 12 μm, respectively. The blood vessel diameter in the mouse retina was in the range of 30.0±6.7 μm for arterioles and 46.5±16.5 μm for venules. The thickness of the mouse retina is about 200-250 μm, so the depth of field of the OCT system 100 was set at 300 μm. The oversampling factor (OF) of the tomograms was calculated for high-speed imaging to minimize the in-frame image blur and between-frame displacement, and thus minimize the effect of eye movements to enable robust observation of transient blood flow responses correlated with retinal light stimulation. The OF was defined as OF=w·N/d, where w is the spot size, N is the number of sampling points, and d is the geometric width of the tomogram. In this study, 2,000 sampling points were used for in vivo measurements, and a scan width of approximately 9.42 mm, leading to an OF of approximately 2.55. The measured optical power of the incident beam on the mouse cornea was below 1 mW, which met safety requirements.

The experiment was conducted in a dark room with no ambient light. The mice were dark-adapted for 1-2 hours prior to the experiment. Following anesthesia, the mouse was moved to the animal holder after 10-15 minutes for acclimatization and full pupil dilation, and the head was fixed using an ear bar and bite bar. The eye was positioned around the optic nerve head area for OCT imaging. The total OCT recording time was 30 s in each experiment, including a 3-s pre-stimulation phase, a 5-s light stimulation phase, and a 22-s post-stimulation phase. OCT recording was performed continuously during the entire session. For the neural-IOS and hemodynamic-IOS measurements, the OCT B-scan recording speed was 35 fps and a total of 1050 frames were acquired. All data were saved to a computer hard drive for post-processing. The OCT system 100 was controlled by software written in LabVIEW (LabVIEW 2013, offered by National Instruments).

Figure 2:
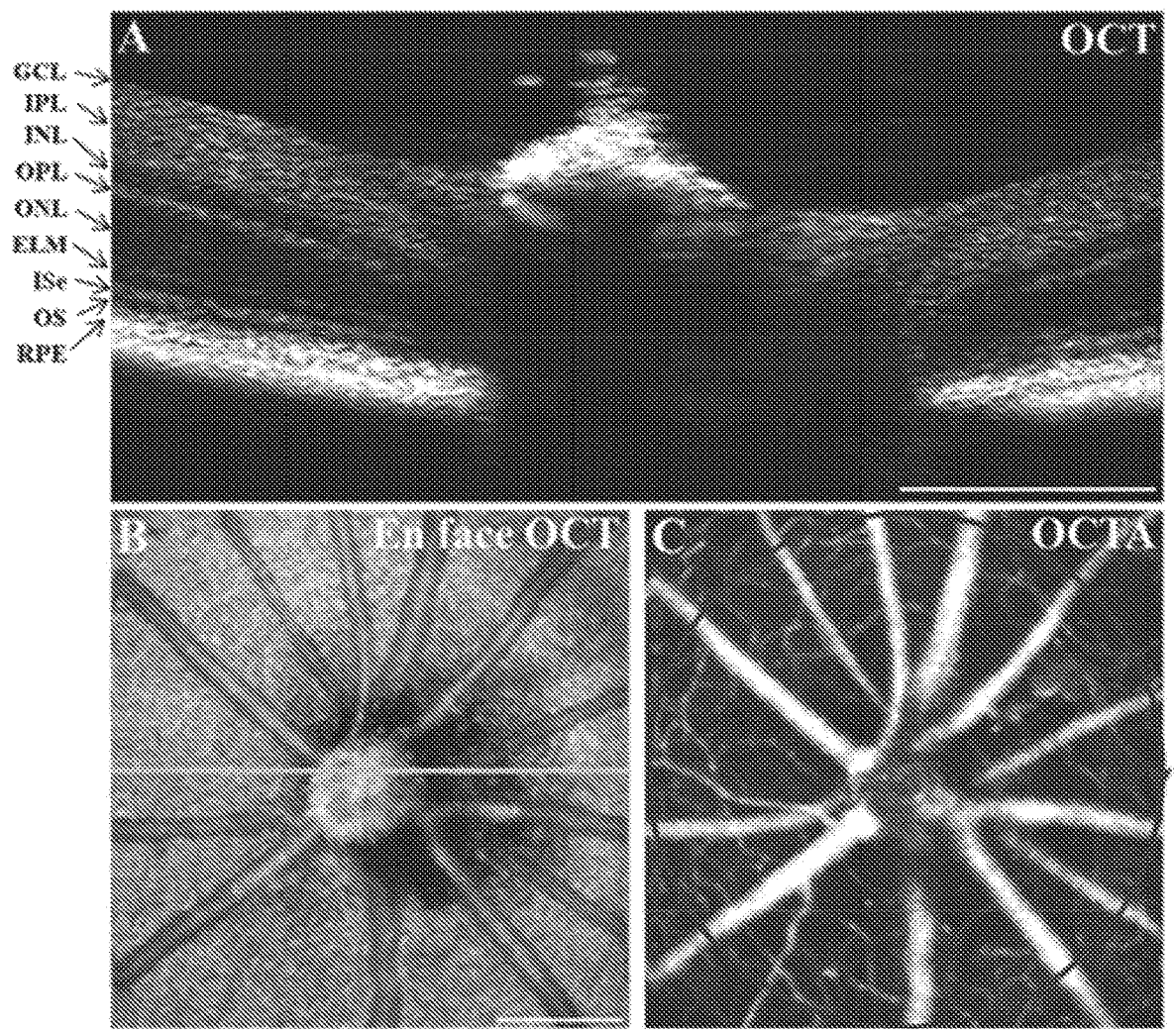
FIG. 2 illustrates OCT and OCTA images acquired by the OCT system shown in FIG. 1 for quantitative assessment of neural-IOSs and hemodynamic-IOSs simultaneously.

FIG. 2 illustrates OCT and OCTA images acquired by the OCT system 100 to demonstrate the retinal structure and vasculature using the OCT system 100. As is known in the art of OCT imaging, an "OCT image" is retina structure image, whereas an "OCTA image" is a retina angiography image. As referred to herein, "OCT image data" is data that defines one or more OCT images and "OCTA image data" is image data that defines one or more OCTA images. In accordance with a representative embodiment, the OCT system 100 acquires OCT image data that is further processed to obtain OCTA image data. Both the OCT image data and the OCTA image data are used to assess concurrent stimulus-evoked neural activity and hemodynamic responses at capillary resolution, as will be described below in more detail with reference to FIG. 7.

The image labeled "A" in FIG. 2 is an OCT image. The image labeled "B" in FIG. 2 is an en face OCT image. The image labeled "C" in FIG. 2 is an OCTA image. In the OCT image A, the individual layers in the mouse retina are clearly differentiated from one another, including the ganglion cell layer (GCL), the inner plexiform layer (IPL), the inner nuclear layer (INL), the outer plexiform layer (OPL), the outer nuclear layer (ONL), the external limiting membrane (ELM), the inner segment ellipsoid (ISe), the outer segment (OS), and the retinal pigment epithelium (RPE). The en face OCT image B provides clear visualization of the large blood vessels. The OCTA image C provides vascular information for both the large blood vessels and small capillaries. For the experiment, an imaging area with a 2 mm diameter around the optic nerve head was chosen to investigate retinal neural activities and hemodynamic responses simultaneously induced by the visible light flicker stimulation.

Figure 3:
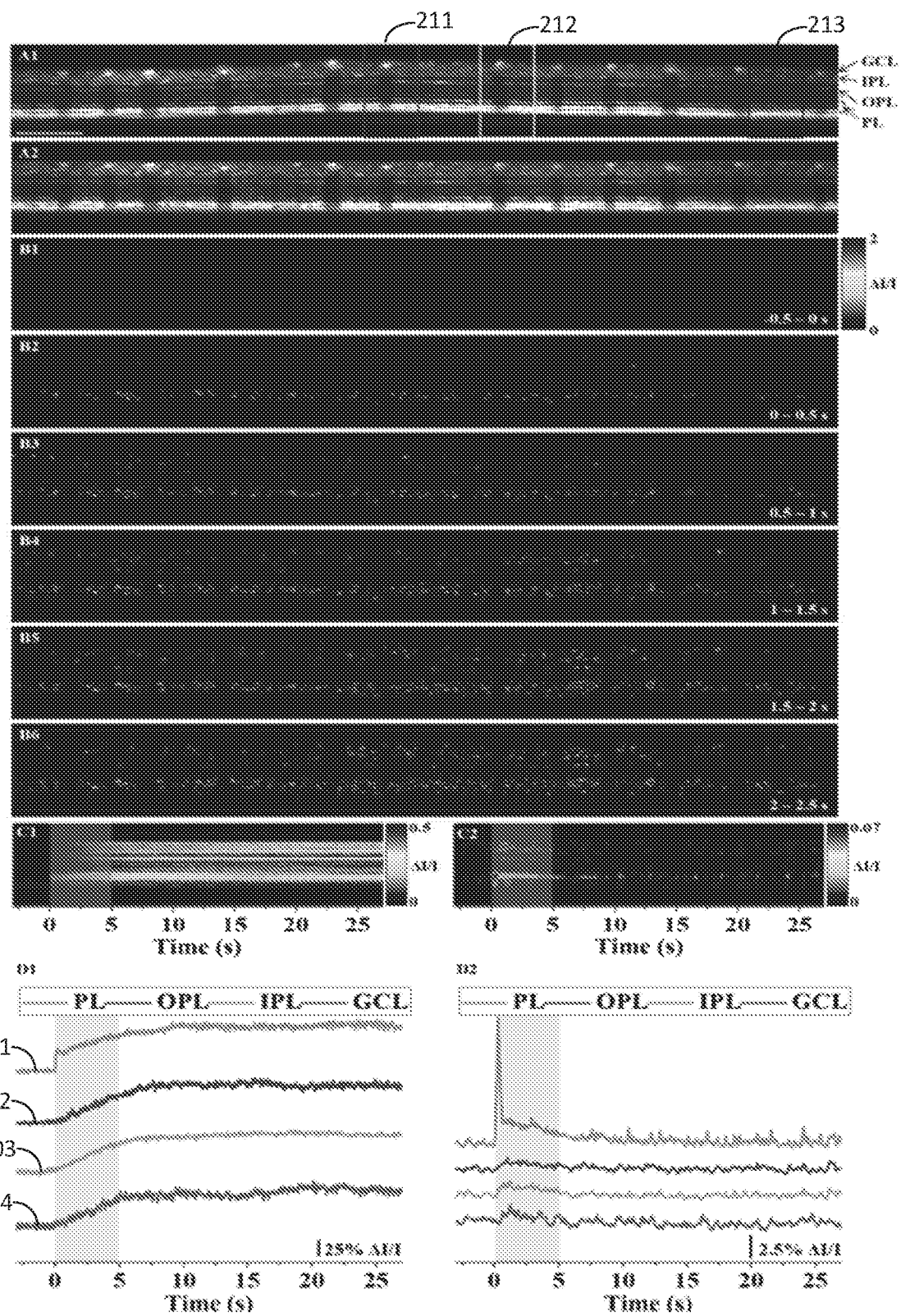
FIG. 3 illustrates an OCT image acquired by the OCT system shown in FIG. 1 and illustrates results of various signal processing algorithms performed on the OCT image to enable neural-IOS activity to be analyzed.

FIG. 3 illustrates an OCT image acquired by the OCT system shown in FIG. 1 and illustrates results of various signal processing algorithms performed on the OCT image to enable neural-IOS activity to be analyzed. The visible light flicker stimuli (e.g., visible light pulses of 100 ms, duty ratio 50%, 10 Hz, 5 s duration, 504±13.5 nm, approximately 460 lux at the corneal surface) were delivered to the retina and each stimulus reliably generated neural-IOSs, indicative of an IOS increase in each retinal layer. The OCT image labeled "A1" in FIG. 3 provides information on the structure of the individual retinal layers, but no information on their vasculature. The OCT image A1 was flattened by realigning each A-line to obtain the flattened OCT image labeled "A2" in FIG. 3. The flattened OCT image A2 allows subsequent signal processing of each retinal layer to be performed reliably.

The processed image data labeled "B1"-"B6" corresponds to spatial neural-IOS maps obtained for different time periods with the pre-stimulus baseline subtracted. The neural-IOS maps demonstrate neural-IOS changes in the individual retinal layers, but not in the vascular regions, in response to the stimuli during different time periods.

The processed image data labeled "C1" in FIG. 3 comprises a differential M-scan tomogram of neural-IOSs for the individual layers generated by processing the flattened OCT image A2. The differential M-scan tomogram C1 demonstrates the spatiotemporal dynamics of neural-IOS changes in the individual retinal layers. It can be seen that rapid neural-IOS changes occur almost immediately in the PL, and gradually in the OPL, IPL and GCL.

The graph labeled "D1" in FIG. 3 shows averaged spatiotemporal curves 201, 202, 203 and 204 for the PL, OPL, IPL and GCL, respectively. The early-phase neural-IOS changes occurred 29 ms after stimulus onset in the PL. In contrast, the later-phase neural-IOS changes were observed between 0.47–0.57 s in the inner retina layers after stimulus onset and gradually increased to reach peak values at different time points.

The processed image data labeled "C2" in FIG. 3 comprises a differential M-scan tomogram of neural-dIOSs that was generated from the flattened OCT image A2 to simultaneously observe the temporal dynamics of neural-IOSs in multiple retinal layers. The differential M-scan tomogram C2 shows pronounced neural-dIOSs in the PL almost immediately after the stimulus onset and then a slow decrease to baseline in the remaining stimulus time period. In contrast, the neural-dIOSs from the inner retina layer, the OPL, the IPL, and the GCL, indicate relatively slow time courses and are sustained for the duration of the stimulus.

The graph labeled "D2" in FIG. 3 shows the quantitative difference in neural-dIOSs between each retinal layer for the differential M-scan tomogram C2. Both neural-IOSs and neural-dIOSs were consistently observed in individual retinal layers (C1 and C2) almost immediately after the stimulus onset and then a slow decrease to baseline in the remaining stimulus time period.

Figure 4:
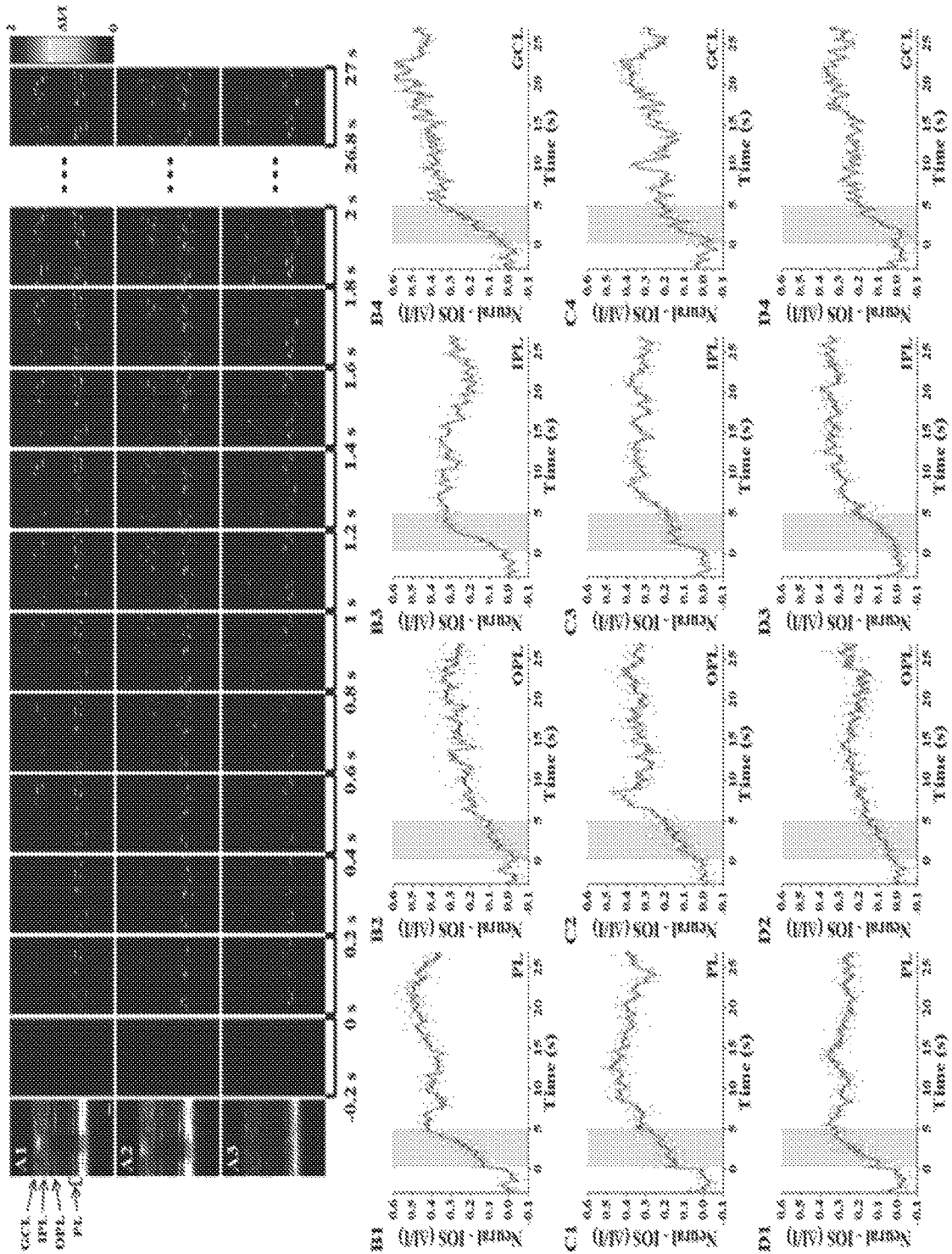
FIG. 4 illustrates local neural IOSs from the portions of the OCT image A1 contained in the boxes labeled 211, 212 and 213 in FIG. 3 and various analyses performed on the OCT image data.

FIG. 4 illustrates local neural IOSs from the portions of the OCT image A1 contained in the boxes labeled 211, 212 and 213 in FIG. 3 and various analyses performed on the OCT image data. In FIG. 4, OCT image portions A1, A2 and A3 correspond to the OCT image portions contained in boxes 211, 212 and 213, respectively. The corresponding spatial neural-IOS maps obtained for different time periods are arranged laterally in FIG. 4 beside the respective OCT image portions A1, A2 and A3. Local neural-IOSs were observed in the PL, OPL, IPL, and GCL except for in the vascular regions. The quantitative characteristics of the localized neural-IOSs for the OCT image portion A1 are represented in the temporal curves labeled "B1" through "B4" in FIG. 4. The quantitative characteristics of the localized neural-IOSs for the OCT image portion A2 are represented in the temporal curves labeled "C1" through "C4" in FIG. 4. The quantitative characteristics of the localized neural-IOSs for the OCT image portion A3 are represented in the temporal curves labeled "D1" through "D4" in FIG. 4.

In the PL, an immediate onset of neural-IOS activity was observed in all three local neural-IOSs represented by temporal curves B1, C1, and D1, but overall the waveforms were variable. The neural-IOSs from the OPL showed different time courses; one showed a slightly delayed onset (temporal curve B2), but the others did not (temporal curves C2 and D2). At the IPL, neural-IOSs were observed to have different temporal characteristics. Similar to the OPL, a slightly delayed onset (temporal curve C3) and non-delayed onset (temporal curves B3 and D3) were also observed. Peak time differences were also observed. Some of the temporal curves reached peak values after the stimulus period (temporal curves C3 and D3), while others reached peak values during the stimulus (temporal curve B3). The neural-IOSs from the GCL also showed different time courses of onset/peak time between the areas that contained large blood vessels (temporal curves B3 and C3).

Figure 5:
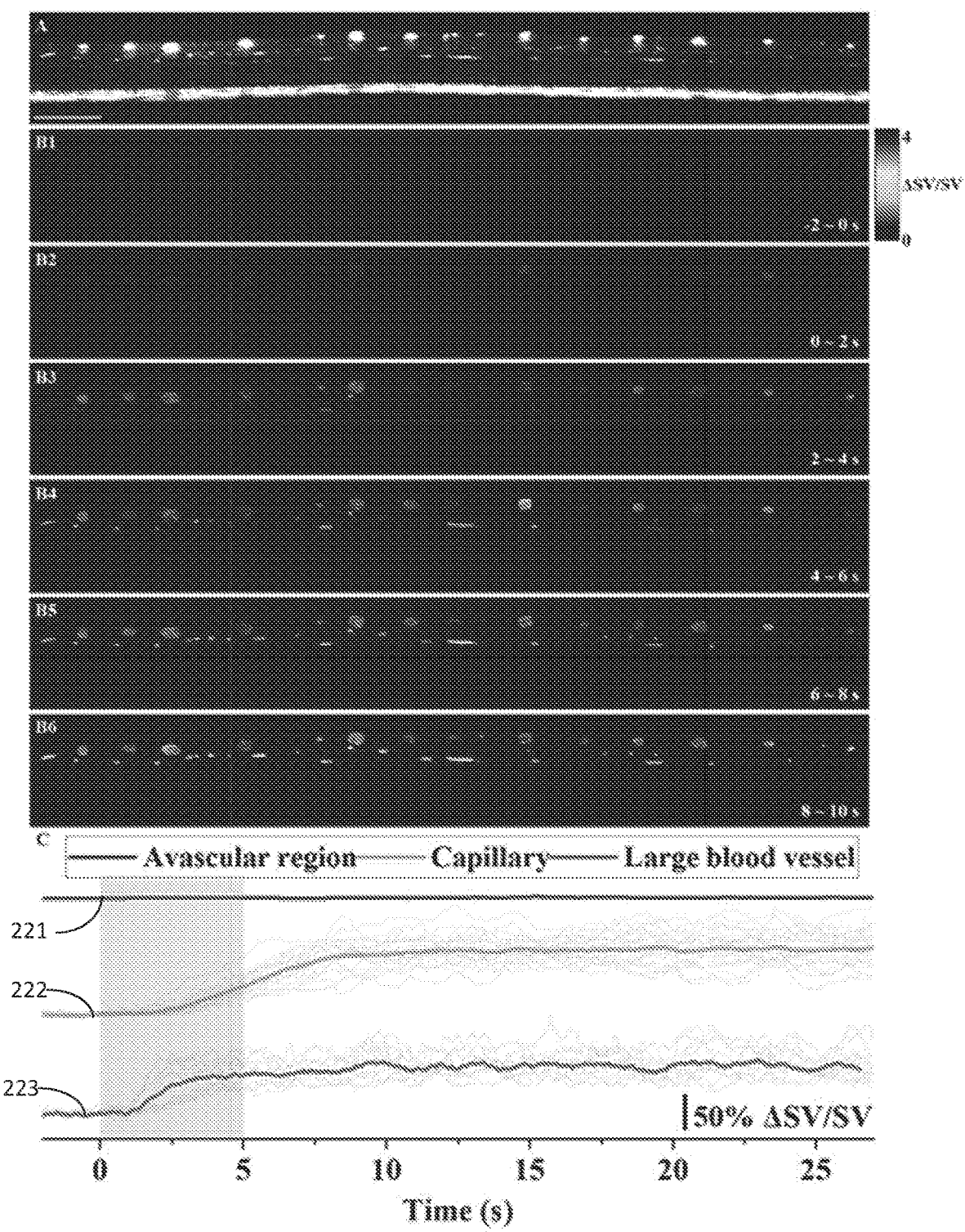
FIG. 5 illustrates OCTA images, labeled "A," spatial hemodynamic-IOS maps for different time periods with the pre-stimulus baseline subtracted, labeled "B1"-"B6", and a plot labeled "C" of temporal curves showing temporal hemodynamic-IOS changes in large blood vessels, capillaries, and avascular regions.

FIG. 5 illustrates OCTA images, labeled "A," spatial hemodynamic-IOS maps for different time periods with the pre-stimulus baseline subtracted, labeled "B1"-"B6", and a plot labeled "C" of temporal curves 221, 222 and 223 showing temporal hemodynamic-IOS changes in large blood vessels, capillaries, and avascular regions. The solid color lines and corresponding dim color line indicate the averaged signal and each single signal, respectively. The OCTA images A were used to reconstruct hemodynamic- IOSs based on speckle variance (SV) calculations with consecutive images from the same OCT image sequence shown in FIGS. 3 and 4. The vascular information was clearly observed in individual retinal layers of the OCTA images, while avascular regions provided almost totally clean backgrounds. In the OCTA images A, it was observed that all large blood vessels were located in the GCL, while capillaries were observed in both the IPL and OPL; blood vessels were also observed in the choroidal layer.

Hemodynamic-IOSs were reconstructed to investigate hemodynamic changes, corresponding to visible light flicker-evoked neural-IOS activation. The hemodynamic-IOS maps, B1-B6, provide local hemodynamics, including blood flow, vessel size, and vessel location at different time points, with the degree of blood flow indicated by differences in lightness (large changes in hemodynamic-IOSs) to darkness (small changes in hemodynamic-IOSs). In the plot C, the large blood vessels and small capillaries were differentiated to verify the effect of vessel size on hemodynamic-IOS responses. Curve 222 represents capillaries and curve 223 represents large blood vessels.

In order to generate the curves 221, 222 and 223, a known intensity thresholding-based segmentation method was used with averaged OCTA images. Twelve large blood vessels and twenty-five small capillaries were extracted and six avascular regions were manually selected. As is evident from the changes in the curves 222 and 223, a noticeable increase in hemodynamic-IOS changes was observed in both large blood vessels and small capillaries. Compared to the onset of neural-IOS changes correlated with visible light stimuli, the onset of the hemodynamic-IOS change was delayed in both large blood vessels and small capillaries, with onset times of $1.23 \pm 0.35$ s and $2.21 \pm 0.7$ s, respectively (n=7 mice). The increased hemodynamic-IOSs were sustained even in the post-stimulation phase. This finding correlated well with that in a previous study by Son, T. et al. described in "Optical coherence tomography angiography of stimulus evoked hemodynamic responses in individual retinal layers." *Biomed Opt Express* 7, 3151-3162, doi:10.1364/boe.7.003151 (2016). In that study, the hemodynamic changes were monitored in the individual retinal layers induced by flickering light stimulation and different hemodynamic responses were observed in the individual retinal layers, probably because of their different metabolic demands, with significant increases in the GCL, IPL and OPL when compared with other layers, as well as delayed onset.

Figure 6:
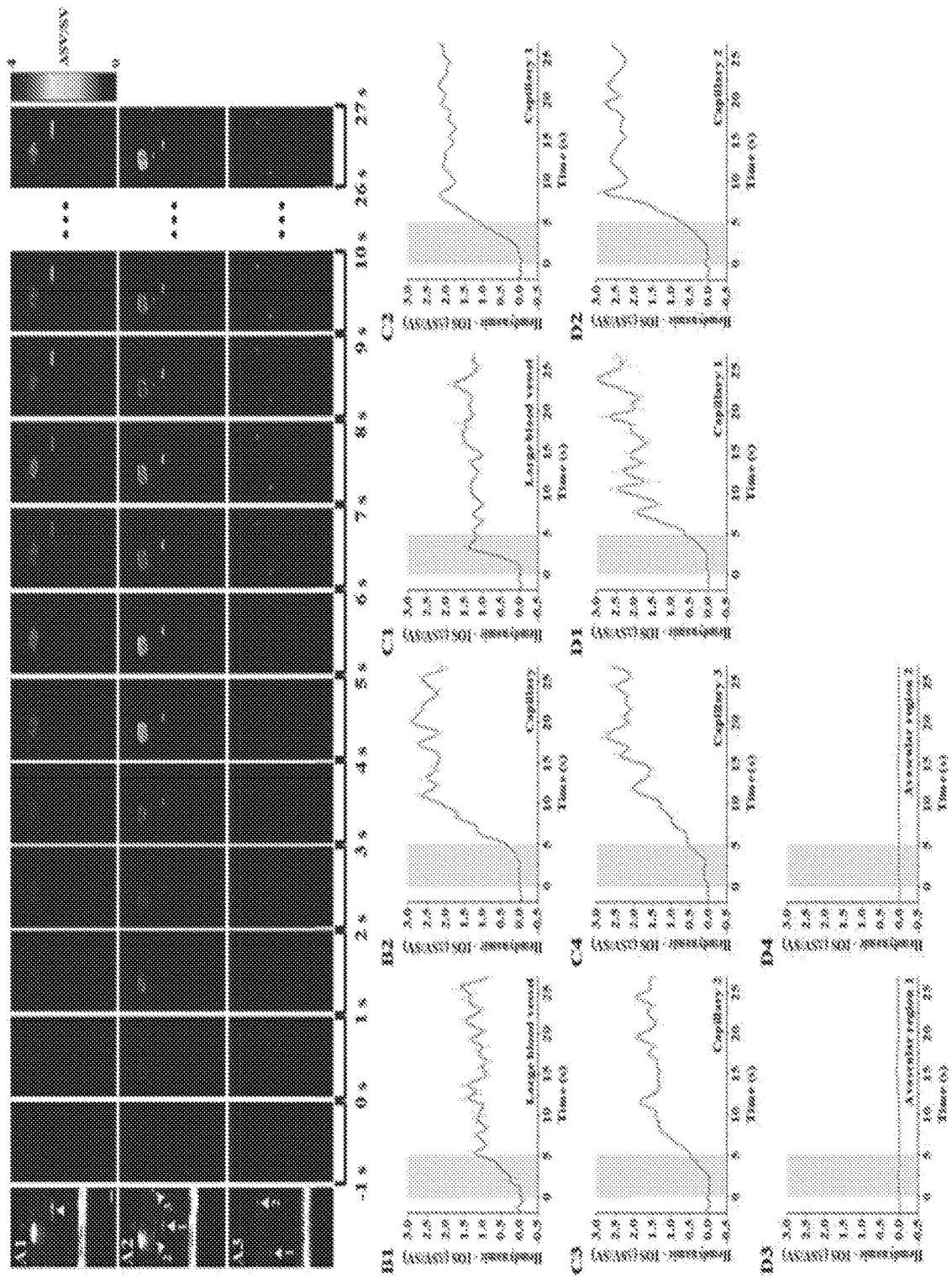
FIG. 6 illustrates three enlarged spatiotemporal images A1, A2 and A3 of in vivo hemodynamic-IOS images in three representative regions corresponding to the same regions as images A1, A2 and A3, respectively, shown in FIG. 4.

FIG. 6 illustrates three enlarged spatiotemporal images A1, A2 and A3 of in vivo hemodynamic-IOS images in three representative regions corresponding to the same regions as images A1, A2 and A3, respectively, shown in FIG. 4. The triangles indicate large blood vessels and capillaries. The corresponding spatial hemodynamic-IOS maps obtained for different time periods are arranged laterally in FIG. 6 beside the respective enlarged spatiotemporal images A1, A2 and A3 images. FIG. 6 also shows Hemodynamic-IOS curves, labeled B, C and D, from different vascular/avascular regions corresponding to images A1, A2, and A3, respectively.

The enlarged hemodynamic-IOS images A1, A2 and A3 have exactly the same locations as those marked in OCT image A1 of FIG. 4. These enlarged hemodynamic-IOS images allowed clearer visualization of hemodynamic-IOS changes at the different time points and locations corresponding to the large blood vessels and small capillaries located in the OCTA images. The hemodynamic-IOSs in the large blood vessels showed a slightly delayed onset time and reached their peak value during the stimulus, whereas a further delayed onset time and peak value were observed in the small capillaries. Quantitative hemodynamic-IOS curves showed different onset/peak times at 1.57/5.34 s and 1.34/3.2 s, respectively, between large blood vessels (temporal curves B1 and C1). The onset and peak time course of neural-IOSs from the GCL (FIG. 4, temporal curves B4 and C4) were similar to those for hemodynamic-IOSs from the large blood vessels. The temporal curves for hemodynamic-IOSs from the small capillaries showed further delayed onset (2.06-3.4 s) and peak times (7.6-11.86 s) compared to that of the large blood vessels (FIG. 6, temporal curves B2, C2, C3, C4, D1, and D2).

From the foregoing discussion, it can be seen that the OCT system 100 is a multi-modal functional OCT imaging system that enables functional monitoring of coherent interactions between neural activities and hemodynamic changes. Thus, the OCT system 100 achieves functional IOS imaging of neurovascular coupling interactions at individual retinal layers with single capillary level resolution. For reliable dissection of neural-IOSs and hemodynamic-IOSs, OCTA-guided IOS data processing was used to separate neural-IOS and hemodynamic-IOS changes precisely. The manner in which this separation is achieved will now be described with reference to FIG. 7.

Figure 7:
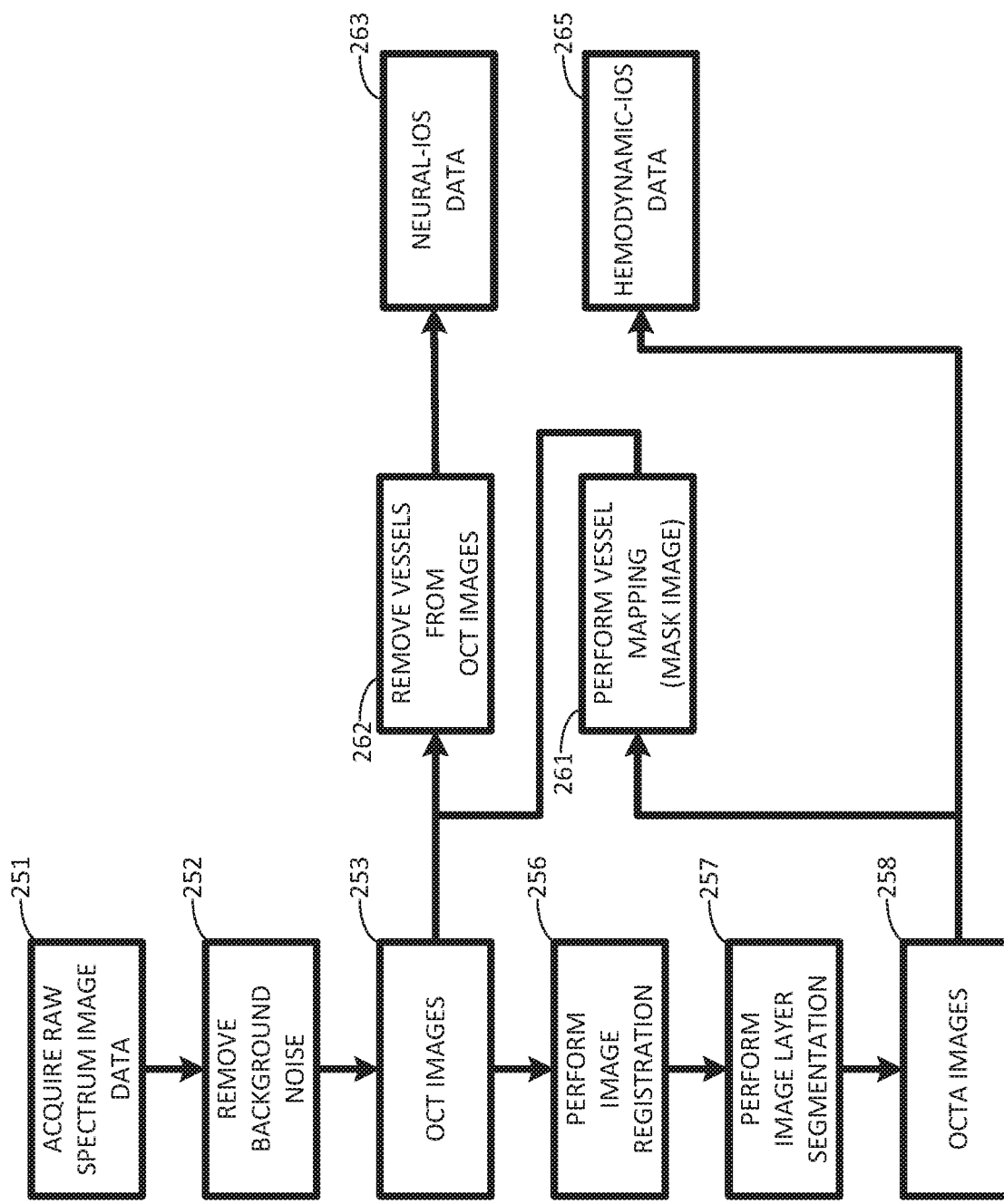
FIG. 7 is a flow diagram that demonstrates the method in accordance with an embodiment.

FIG. 7 is a flow diagram that demonstrates the method in accordance with an embodiment. The first step is the acquisition of the raw spectrum image data by the OCT system 100, as indicated by block 251. The raw spectrum image data generally corresponds to OCT image data, but it typically contains noise. Block 252 represents the step of performing one or more image processing algorithms (e.g., filtering) to remove background noise. At this point, the images are deemed to be OCT images 253 similar to the OCT images A1 shown in FIG. 3. As discussed above with reference to FIGS. 2-6, the information pertaining to neural-IOS activity is obtained from the OCT images and from the OCTA mask images, whereas the information pertaining to hemodynamic response is obtained from the OCTA images. Because the neural-IOS activity is determined based on both the OCT images and on the OCTA mask images, the neural IOSs are referred to herein as being determined via OCTA-guided OCT data processing.

Before the neural-IOS data can be obtained, the OCTA images are generated during the steps represented by blocks 256-258. At block 256, an image registration algorithm is performed on the OCT images 253. The image registration algorithm is applied to compensate for bulk motion between the sequential images acquired by the OCT system 100. The image registration algorithm comprises a cross-correlation algorithm and a rigid body transformation algorithm that are used to achieve sub-pixel accuracy. At block 257, an image layer segmentation algorithm is performed to localize the intra-retinal boundaries of each individual layer. A known optimal graph search algorithm may be used for this purpose. The result of the algorithms represented by blocks 256 and 257 are OCTA images 258 similar to the OCTA image C shown in FIG. 2.

Once the OCTA images 258 have been obtained, a vessel mapping algorithm is performed to map blood vessels in the OCTA images 258, as indicated by block 261. This results in masks that will be used to remove the blood vessels from the OCT images. At the step represented by block 262, a vessel rejection algorithm is performed during which the masks generated at block 261 are used with the OCT images 253 to remove blood vessels from the OCT images 253. This produces the final neural-IOS data 263 that may be analyzed in the manner discussed above with reference to FIGS. 3 and 4. The OCTA images 258 contain the hemodynamic-IOS data represented by block 265 and may be directly analyzed in the manner discussed above with reference to FIGS. 5 and 6.

A variety of modifications may be made to the method described above with reference to FIG. 7 and all such modifications are within the scope of the inventive principles and concepts being described herein. Some modifications to the method described above with reference to FIG. 7 were made during the actual experiment, as will now be described. As indicated above, the OCT images are reconstructed from the acquired raw spectrum data. The image registration algorithm represented by block 256 was applied to compensate for bulk motion between the sequential images. As indicated above, in accordance with this embodiment, the image registration algorithm uses a cross-correlation algorithm and conducted rigid body transformation to achieve sub-pixel accuracy. The thickness of the layer was not homogeneous even in the same layer depending on the location, so the thickness of each layer was equalized. The boundaries of each layer were detected using intensity and texture methods based on the image layer segmentation algorithm represented by block 257. In accordance with this embodiment, the image layer segmentation algorithm includes a flattening algorithm. The mean column pixel number of the segmented layer was calculated and then each column was spatially transformed, having the same values (mean column pixel number) as those using the bicubic interpolation method. This spatial transformation of each column was performed with all other layers to obtain flattened OCT images, and consequently, flattened OCTA images at block 258. The flattening algorithm may instead be performed at some point in time between blocks 251 and 253 such that the OCT image 253 that is processed at block 262 is a flattened OCT image.

At the step represented by block 262, the blood vessels were separated in the OCT images to obtain only neural-IOSs. A previous known study used a dynamic spatiotemporal filtering algorithm to remove the hemodynamic signal from confocal IOSs. In accordance with this embodiment, the blood vessels were segmented using the masks generated from the flattened OCTA images at block 261. By using the masks, the blood vessels in each OCT image were forced to zero at block 262 to produce the neural-IOS data 263.

The basic procedures used for processing the neural-IOS data 263 to obtain the results described above with reference to FIGS. 2 and 3 were as follows: the pre-stimulus images were averaged pixel by pixel (background intensity I); the background intensity I was subtracted from each image, pixel by pixel, and the dynamic change ΔI was calculated; and the image sequence of ΔI/I was used to reconstruct the neural-IOS images. A differential M-scan tomogram was calculated to improve the visibility of the stimulus-induced neural-IOS changes. Every neural-IOS image was averaged toward the column direction and combined to generate a differential M-scan tomogram. Next, neural-dIOSs were calculated to show active neural-IOS changes by removing background optical signals. The neural-dIOS calculation method shares the same equation as that used for neural-IOS calculations, except that the averaged pixel value of consecutive images before the current image was used as a baseline I and the next consecutive averaged images were used to calculate the dynamic change ΔI. For the neural-dIOSs discussed above, twenty to twenty-five images were selected for the baseline I and dynamic change ΔI, respectively.

Another modification to the method described above with reference to FIG. 7 is that, in the experiment, the OCT images 253 were processed in accordance with a speckle variance (SV) algorithm to calculate OCTA images. The SV algorithm was applied in between block 256 and block 258. Although a conventional SV algorithm could have been used, in accordance with this embodiment, a custom SV algorithm was used. Conventional SV calculations use discrete image frames, whereas the custom SV algorithm used a consecutive SV calculation approach, as will now be described. Each OCTA image was calculated using thirty-five frames of the OCT images, with two consecutive OCTA images sharing thirty-four frames of OCT images (i.e., the starting frame of an OCTA image was one frame later than that of the immediate previous OCTA image). These conventional and custom SV algorithms use the same calculation equation:

$$SV_{ijk} = \Sigma_i [I_{ijk}(x,z) - \Sigma_i I_{ijk}(x,z)]] = \Sigma_i [I_{ijk} - I_{mean}]$$

However, the frames used for the calculations are different. The consecutive SV calculation approach can produce higher temporal resolution of OCTA images than the conventional SV calculation approach.

Following the OCTA calculation, entire OCTA images were averaged according to the frames to generate the masks at block 261. The blood vessels were extracted using an intensity thresholding-based image segmentation method from the masks generated at block 262. The OCTA images were normalized by the average of the pre-stimulation images for each individual OCTA image, and a hemodynamic-IOS image was generated as ΔSV/SV, where SV was the intensity of SV for each frame within a depth scan and ΔSV was the difference between the intensity of the SV in each frame and the time-averaged intensity of SV determined from the pre-stimulation depth scans. Hemodynamic-IOSs and mask images were then obtained from the OCTA images and combined to extract signals from vessel regions only to minimize effects from the background areas. Since the hemodynamic-IOSs were from a blood vessel, it was strongly affected by the pulse and showed a periodic peak. Savitzky-Golay filtering (polynomial order 2; window length 30) was applied to the hemodynamic-IOSs for signal denoising.

It should be noted some of the steps described above with reference to FIG. 7 may be rearranged, modified and/or deleted altogether while still achieving the goals of the inventive principles and concepts. The processes or algorithms described above that are represented by the blocks shown in FIG. 7 are typically performed in software, firmware and/or hardware or a combination thereof. The software, firmware or combination thereof is typically stored in some type of non-transitory computer-readable medium, such as, for example, a solid state storage device (e.g., read only memory (ROM), random access memory (RAM), flash memory, erasable programmable ROM (EPROM)), optical storage devices, magnetic storage devices, etc. A processor executes the computer instructions. The processor may be any suitable computational device such as, for example, one or more microprocessors, microcontrollers, application specific integrated circuits (ASICs), field programmable gate arrays (FPGAs), programmable logic arrays (PLAs), or a combination thereof.

Figure 8:
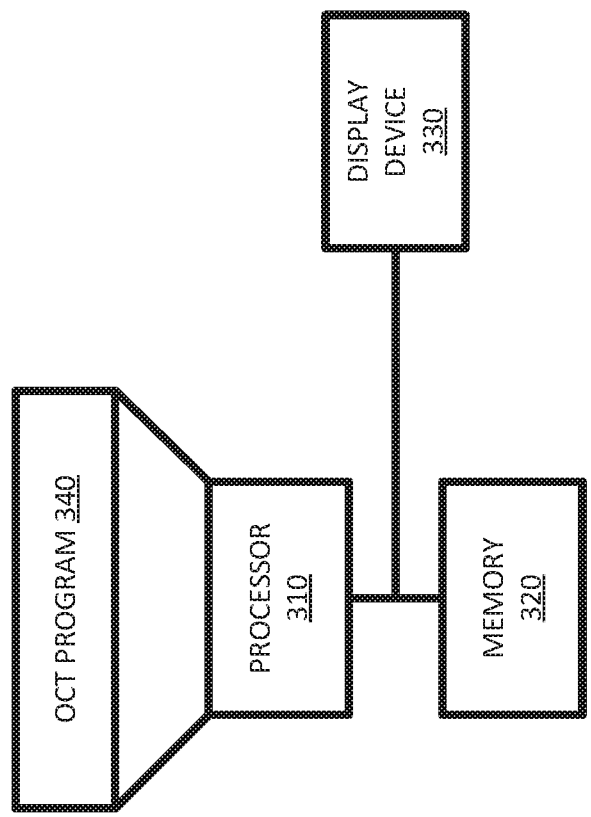
FIG. 8 is a block diagram of a computer system in accordance with an embodiment that receives the output of the sensor array shown in FIG. 1 and processes it to perform the analyses depicted in FIGS. 1-7.

FIG. 8 is a block diagram of a computer system 300 in accordance with an embodiment that receives the output of the sensor array 157 shown in FIG. 1 and processes it to perform the analyses described above with reference to FIGS. 1-7. The computer system 300 includes a processor 310 that is configured to perform the algorithms described above and a memory 320 that stores computer code that is executed by processor 310. The computer system 300 also includes a display device 330 that is in communication with the processor 310 and with the memory 320. The processor 310 executes an OCT program 340 to perform the tasks described above with reference to FIG. 7.

In summary, the above demonstrates an OCT imaging system and method that achieve concurrent functional OCT imaging of neural-IOS and hemodynamic-IOS changes in response to flickering light stimulation. OCTA-guided OCT data processing dissected vascular (i.e., blood vessel) and avascular (i.e., neural tissue) retinal areas reliably, enabling robust neural-IOS and hemodynamic-IOS monitoring simultaneously. This provides a noninvasive imaging platform for high-speed and high-resolution study of the functional relationship between retinal neural degeneration and vascular pathology, promoting early detection and therapy development of neurodegenerative diseases.

It should be noted that the inventive principles and concepts have been described with reference to representative embodiments, but that the inventive principles and concepts are not limited to the representative embodiments described herein. Although the inventive principles and concepts have been illustrated and described in detail in the drawings and in the foregoing description, such illustration and description are to be considered illustrative or exemplary and not restrictive; the invention is not limited to the disclosed embodiments. Other variations to the disclosed embodiments can be understood and effected by those skilled in the art, from a study of the drawings, the disclosure, and the appended claims.

What is claimed is:

1. A multi-modal optical coherence tomography (OCT) system configured to provide dynamic mapping of hemodynamic responses, the system comprising:
    a light source;
    a coupler;
    a sample arm comprising:
        at least one scanning mirror,
        a dichroic mirror, and
        a retinal stimulator that generates flicker light stimulation coupled into at least one eye of a subject through the dichroic mirror;
    a reference arm;
    a spectrometer;
        wherein the coupler divides a light beam coming from the light source into a sample light beam directed to the sample arm and a reference light beam directed to the reference arm;
        wherein the sample light beam passes through the at least one scanning mirror and is coupled into the at least one eye of the subject by the dichroic mirror; and
        wherein the spectrometer receives an interference spectrum returning from the sample and reference arms; and
    processing circuitry including a processor and a memory having program instructions that, when executed by the processor, cause the multi-modal OCT system to:
    acquire raw spectrum image data from the spectrometer;
    generate OCT images from the raw spectrum image data; and
    process the OCT images to map hemodynamic responses of the eye evoked by the flicker light stimulation.

2. The multi-modal OCT system of claim 1, wherein the program instructions, when executed by the processor, further cause the multi-modal OCT system to: process the OCT images to dynamically map neural activity of the eye evoked by the flicker light stimulation.

3. The multi-modal OCT system of claim 2, wherein the map of hemodynamic responses is a hemodynamic-intrinsic optical signal (IOS) map and the map of neural activity is a neural-IOS map.

4. The multi-modal OCT system of claim 1, wherein the program instructions, when executed by the processor, further cause the multi-modal OCT system to:
    obtain OCT angiography (OCTA) images by processing the OCT images;
    generate blood vessel masks using the OCTA images; and
    obtain a functional neural IOS map by processing the OCT images with the blood vessel masks to remove blood vessels from the OCT images.

5. The multi-modal OCT system of claim 4, wherein the program instructions, when executed by the processor, further cause the multi-modal OCT system to: process the OCTA images to generate a hemodynamic-IOS map.

6. The multi-modal OCT system of claim 2, wherein the neural activity that is mapped includes neural activity of multiple cell layers of the eye, wherein the multiple cell layers include at least two of the ganglion cell layer, the inner plexiform layer, the outer plexiform layer and the choroid layer.

7. The multi-modal OCT system of claim 4, wherein hemodynamic response data is obtained from the OCTA images.

8. The multi-modal OCT system of claim 1, wherein the multi-modal OCT system is one of a spectral domain OCT system, a swept source OCT system, a point scanning OCT system, a line scan OCT system and a full field OCT system.

9. The multi-modal OCT system of claim 1, further comprising:
    a line CCD camera;
    a diffraction grating; and
    a lens, wherein the line CCD camera has a line rate up to 70,000 Hertz (Hz).

10. The multi-modal OCT system of claim 1, wherein the multi-modal OCT system has a wide depth of field compared to a thickness of a retina of the subject.

11. The multi-modal OCT system of claim 1, wherein the light source is a near infrared superluminescent diode.

12. The multi-modal OCT system of claim 1, wherein the light source is one of a superluminescent diode, a swept source laser, and a supercontinuum laser.

* * * * *